United States Patent [19]
Knight, Jr.

[11] 3,958,936
[45] May 25, 1976

[54] PLASTICS STERILIZER AND MELTER HAVING AN AFTERBURNER

[75] Inventor: Philip A. Knight, Jr., Concord, Mass.

[73] Assignee: Raytheon Company, Lexington, Mass.

[22] Filed: July 2, 1975

[21] Appl. No.: 592,429

[52] U.S. Cl. ................................. 21/93; 13/20; 21/103; 23/277 R; 23/277 C; 219/421; 219/424; 432/156
[51] Int. Cl.² ................. A61L 3/00; A61L 3/02; F27B 14/06; F27B 14/08
[58] Field of Search ............. 21/93, 102 R, 2, 103, 21/54 R; 23/277 C, 277 R; 432/156, 158; 219/420, 421, 424, 423; 13/6, 20

[56] References Cited
UNITED STATES PATENTS

| | | | |
|---|---|---|---|
| 1,906,799 | 5/1933 | Lobley | 13/20 |
| 2,106,462 | 1/1938 | Lindberg | 219/420 |
| 2,179,256 | 11/1939 | Gill | 21/93 |
| 3,085,001 | 4/1963 | Morris | 23/277 C |
| 3,375,081 | 3/1968 | Papp et al. | 23/277 C |
| 3,440,322 | 4/1969 | Young | 219/424 |
| 3,716,339 | 2/1973 | Shigaki et al. | 23/277 C |
| 3,804,079 | 4/1974 | Schrader | 23/277 C |
| 3,886,854 | 6/1975 | Culpepper | 23/277 C |

*Primary Examiner*—Morris O. Wolk
*Assistant Examiner*—Bradley R. Garris
*Attorney, Agent, or Firm*—Harold A. Murphy; Joseph D. Pannone; John T. Meaney

[57] ABSTRACT

An appliance for sterilizing and melting plastic items such as found in hospitals or the like, for example, which appliance includes a chamber containing a foil casing within which the items are placed, and means for heating the chamber for a temperature and time cycle sufficient to soften or melt the plastic items which when cooled will form a solid body of plastic material containing within it other non-melted disposable items such as might have been included with the plastic items.

8 Claims, 2 Drawing Figures

PLASTICS STERILIZER AND MELTER HAVING AN AFTERBURNER

BACKGROUND OF THE INVENTION

In hospital microbiological laboratories and similar localities an improved method is acutely needed for the disposal of plastic items such as containers used for infected materials. Such items might include Petri dishes which are used for the analysis of bacteriological specimens, urine cups, disposable syringes, and many others.

Past methods of disposal have been by burning the plastic items in an on-site incinerator. However such incinerators do emit undesirable byproducts into the atmosphere and, therefore, have been banned by environmental control agencies.

Present methods of disposal involve transporting the infected plastics through the hospital and storage until subsequently shipped to a suitable dump or landfill area. This procedure is obviously undesirable. In other instances the plastics are sterilized in the lab in an autoclave before subsequent disposal. In the autoclave the infected plastic materials are exposed to steam at about 230°–270°F for about an hour. This produces a wet and objectionably odorous mess since the agar solutions used for analysis are organic.

SUMMARY OF THE INVENTION

The present invention overcomes the above and other objections to known methods for the disposal of infected plastic materials by the use of a heating appliance wherein the materials are subjected to a temperature which will cause the materials to soften or melt so that when cooled there will be formed a single block of hardened plastic which may be easily disposed of in a sanitary landfill, for example.

To aid such disposal, the invention includes the provision of a foil container or bag within the melting chamber of the appliance into which the infected plastic items are deposited before melting. After the plastics are melted and subsequently hardened, the foil container with the block of hardened plastic within it is removed and sealed.

With this invention it is also possible to drop into the container other small items such as needles which will become embedded in the block of plastic for disposal therewith.

While being melted, the infected plastic items will be subjected to selected temperatures ranging from about 400°F to about 600°F for periods of 30 to 90 minutes.

This exposure to heat insures the volatilization of all water and lower temperature organics, the sterilization of all the materials within the container, and the melting of the plastic materials to minimum volume. Non-volatilized organic products and salts which produce odors are substantially encapsulated in the melted plastic and rendered inoffensive.

In further accordance with the invention, vapors, odors, smoke and any other objectionable gases evolved during the melting process are made to pass through an aferburner for incineration of through a catalytic oxidation unit for degradation.

A suitable cycle timer is included in the electrical circuit so that when the appliance is first turned on both burners will operate simultaneously during the melting cycle and at the end of the melting cycle the afterburner will remain on until the conclusion of the cooling cycle.

BRIEF DESCRIPTION OF THE DRAWINGS

The above and other objectives of this invention will become apparent from the following description taken in connection with the accompanying drawings, wherein.

DESCRIPTION OF THE PREFERRED EMBODIMENT

Figure 1:
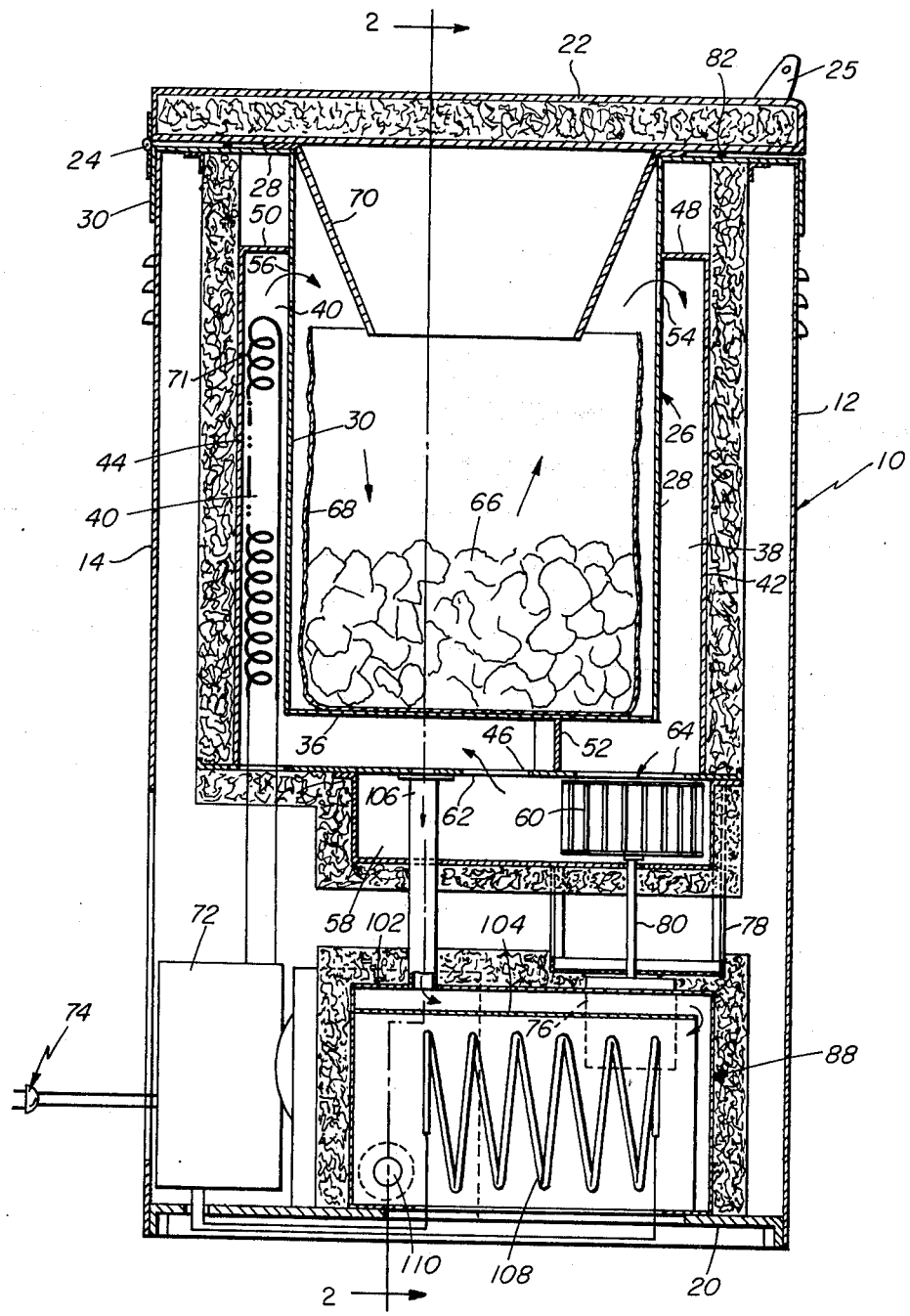
FIG. 1 is a side elevational view partly in section of an appliance embodying the invention.

Referring more particularly to the drawings wherein like characters of reference designate like parts throughout the views, the appliance embodying the invention includes an outer housing or cabinet 10 including front and back walls 12 and 14, opposed side walls 16 and 18, and a base or bottom wall 20. The upper end of the cabinet 10 is covered by a top 22 which is hinged as at 24 to the upper end of the back wall 14 (FIG. 1) and which may be lifted by means of handle 25 to provide access to the interior of the melter.

Inside the cabinet 10 is an open topped melting chamber 26 of relatively heavy gauge sheet metal which is suitably supported as by a flange 28 around its upper end, which flange has a downturned portion 30 overlying and affixed to the upper end of the cabinet. Melting chamber 26 includes front and rear walls 28 and 30, opposing side walls 32 and 34 and a bottom wall 36. As shown in FIG. 1 there are provided two air circulation chambers or compartments 38 and 40 on the outside of the front and back walls of the melting chamber, which compartments each are continuous along the bottom of the melting chamber. The compartments are defined by side walls 42 and 44 and a bottom wall 46 which are fixed at their upper ends to the chamber walls 30 and 28 by top flanges 48 and 50 and are separated beneath the melting chamber by a divider 52.

The front and back walls of the melting chamber 26 are provided in the upper extremities with respective air circulation ports 54 and 56 respectively whereby the compartments are in constant communication with the interior of the melting chamber 26. Beneath the bottom wall 46 is a separate compartment or volute 58 including a blower 60. The blower 60 is disposed to force air through an opening 62 (FIG. 1) into compartment 40 from which it will flow into the melting chamber 26 through port 56. From melting chamber 26 this air is then drawn back to the blower 60 through port 54, compartment 38 and opening 64.

Within the melting compartment are placed a number of plastic articles 66 to be melted and sterilized in accordance with this invention. So that proper disposal of the melted articles can be eventually achieved, these plastic articles are deposited within an open foil bag or container 68 into which the articles may be dropped through a chute or other guide device 70 which is optionally mounted at the top of the chamber beneath the lid 22. The chute 70 is angled downwardly as shown past the inlet port 56 and thus serves not only to prevent spillage into the chamber outside the container 68 but also to deflect air entering through the port 56 downwardly into the container.

In order to melt the plastic materials in the container it is necessary that the incoming air be heated to at least about 450°F. Therefore, an electrical heating element 71 is located in the input air circulation compartment 40 so that the air forced through the compartment 40 into the container 68 by the blower will be heated to the desired extent. Suitable electrical controls for the heating element 71 are mounted in a box 72 in a lower portion of the cabinet 10, and this unit is readily connected to a source of 115-V alternating current as by conventional cord and plug 74.

The melting chamber 26, air circulation compartments 38 and 40 and blower-volute 58–60 are encased in suitable insulation so as to reduce the amount of heat loss into the cabinet. In order to prevent damage to the blower motor 76, it is spaced from the volute by a bracket 78 through which its operating shaft 80 extends.

Thus, when the device is operated, the plastic articles will be reduced to a flowable state in a controlled length of time which may be varied as desired by suitable conventional clock timing means (not shown). A thermostat (also not shown) will be placed in the air circulation system, preferably downstream of the heating element 71, and is connected in a suitable manner to the controls in box 72 to control temperatures during the heating cycle.

When the heating and melting cycle is completed, the chamber is allowed to cool, whereupon the melted plastic materials will become solidified into a single hard block within the foil container, which block contains embedded within it such non-volatilized odor-producing organic products and salts and metal elements which might have been included with the plastic materials.

It will be apparent that during a heating and melting cycle some plastic vapors may be produced in the melting chamber 26. Also, it has been found that various solutions in or on the materials deposited in the chamber 26 will also produce certain organic vapors which could leak through into the atmosphere, even though resilient sealing rings 82 are used between the lid or cover 22 and the top of the cabinet 10.

Figure 2:
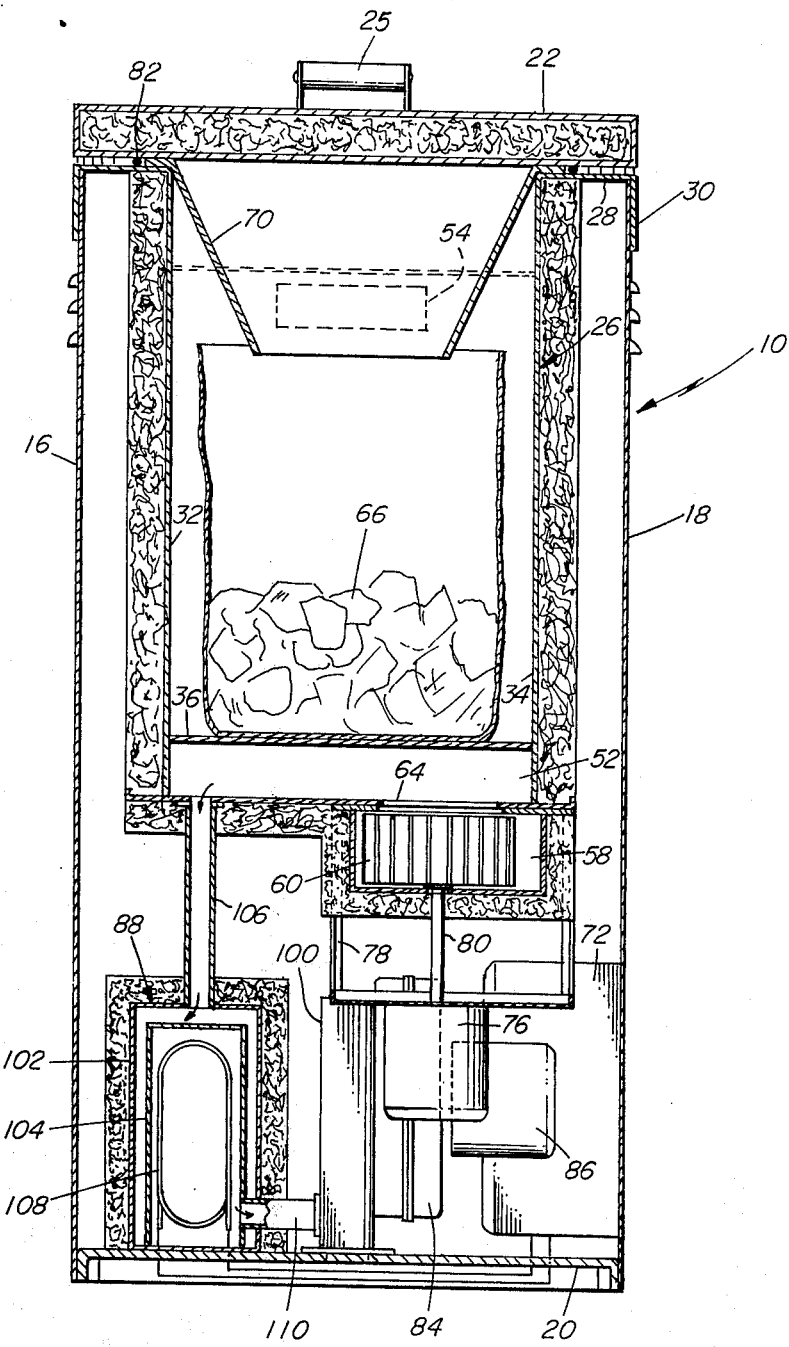
FIG. 2 is a vertical sectional view taken substantially on line 2—2 of FIG. 1.

In order to reduce or eliminate this problem there is provided in the lower portion of the cabinet a second blower unit 84 which is operated by its own motor 86 to draw such vapors out of the system through an afterburner 88 or catalytic burner and a heat diluter 100 (FIG. 2). The afterburner 88 comprises a metal outer chamber 102 which contains within it a second chamber 104 which at one end is closed by an end wall of outer chamber 102 and which is open at its other end, with the open end being spaced from the opposite end wall of the outer chamber 102 as shown. Outer chamber 102 is connected to first air circulation chamber 40 by a pipe 106 which is attached at one end to the top wall of the chamber and at its other end is connected into the air circulation chamber 40 at approximately the point of highest pressure therein.

Within the inner chamber 104 is located a heating element or coil 108 which is suitably connected into the electrical control system. Thus vapors which are drawn out of the air circulation chamber 40 pass through pipe 106 into outer afterburner chamber 102, then flow around the outer surface of the inner chamber 104 and eventually enter the inner chamber through its open end.

The vapors then are made to contact the heating element 108 by any suitable means such as deflectors or space restrictors (not shown) so that the vapors are substantially completely incinerated. The resultant heated air in the inner chamber 104 then passes out through a connecting pipe 110 to the diluter 100 which is a simple box open at its bottom to fit over an opening in the base or bottom 20 of the appliance. Then, when the second blower 84 operates to draw air and vapors from the system as described it will also simultaneously draw into the diluter cool air from beneath the appliance. This cool air mixes with the hot air being drawn from the afterburner so that the air drawn back into the blower unit and eventually exhausted into the atmosphere will not only be free from obnoxious, odorous or otherwise objectionable vapors but will also not be objectionably hot.

The control system may be of any conventional type which may be operated to simultaneously switch on both blower motors 76 and 86 and both heating elements 71 and 108. At the end of a selected heating cycle such as 90 minutes, for example, the plastic materials in the foil container 68 will be sufficiently reduced to a flowable state. At this time the heating element 71 is automatically switched off and the melting chamber is allowed to become cooled, whereupon the plastic material will harden into a unitary block of plastic which may be eventually removed with the foil container from the melting chamber for disposal. During the cool down cycle the second blower unit continues to operate to continuously remove undesirable vapors from the system until the plastic hardens or until the end of a selected time period as set up by the control system, at which time the system is completely switched off.

In order to provide a completely safe appliance, the melting chamber, air circulation chambers, afterburner and all other heated areas are fully insulated as shown. Also, interlocks, (not shown) may be provided to retain the cover closed whenever the system is being operated.

It will be apparent from the foregoing that all of the objectives of this invention have been achieved by the process shown and described. It will also be apparent that various changes and modifications in the structures shown and described may be made by those skilled in the art without departing from the spirit of the invention as expressed in the accompanying claims. Therefore, all material shown and described is to be interpreted as illustrative and not in a limiting sense.

What is claimed is:

1. A furnace for melting and sterilizing plastic items comprising a first housing, a melting chamber within a portion of the first housing, an air circulation system within the first housing comprising a first air circulation chamber on one side of the melting chamber and communicating therewith, a heating element, a second air circulation chamber on the opposite side of the melting chamber and communicating therewith, and blower means connected with both said air circulation chambers for directing air into the first thereof, and consecutively through the heating element and through the melting chamber and through the second air circulation chamber, and afterburner means located outside of the first housing comprising a second housing connected with said air circulation system, heating means within said second housing, and second blower means for drawing some of the air from one of said air circulation chambers through the heating means.

2. A furnace for melting and sterilizing plastic items comprising a first housing, a melting chamber within a portion of the first housing, a first air circulation chamber within the first housing on one side of the melting chamber and having an inlet port communicating with the interior of the melting chamber, a heating element within said first air circulation chamber, a second air circulation chamber within the first housing on the opposite side of the melting chamber and having an outlet port communicating with the interior of the melting chamber, first blower means within the first housing connected with both said air circulation chambers for directing air into the first thereof, through the heating element and into the melting chamber and for simultaneously drawing air out of the melting chamber through the second air circulation chamber, and afterburner means located outside of the first housing comprising a second housing connected with one of said air circulation chambers, second heating means within said second housing, and second blower means for drawing some of the air from one of said air circulation chambers through the second housing and the second heating means thereof.

3. A furnace as set forth in claim 2 wherein said first blower means is connected to said first air circulation chamber to blow air thereinto and to said second air circulation chamber to suction air therefrom, and the second housing is connected to said first air circulation chamber.

4. A furnace as set forth in claim 3 wherein said second housing is connected to said first air circulation chamber at approximately the area of most positive air pressure.

5. A furnace as set forth in claim 3 wherein said second housing includes a first compartment which is connected to said first air circulation chamber, and a second compartment within said first compartment and connected to said second blower means, and wherein said second heating means is located within said second compartment.

6. A furnace as set forth in claim 3 wherein diluter means is located between said second housing and said second blower means and has an opening communicating with the atmosphere external to said furnace whereby cool air is mixed with heated air being drawn from the second housing by the second blower means.

7. A furnace as set forth in claim 2 wherein disposable container means is positioned within the melting chamber for receiving plastic items to be melted, said container means being removable from the melting chamber, whereby after the plastic items have been melted and resolidified, said container means is removed for disposal together with the resolidified plastics therein.

8. A furnace as set forth in claim 7 wherein said container means is a metal foil container.

* * * * *